(12) United States Patent
Goto et al.

(10) Patent No.: US 8,557,259 B2
(45) Date of Patent: Oct. 15, 2013

(54) LIQUID PREPARATION

(75) Inventors: Norio Goto, Honjo (JP); Koichi Shibusawa, Honjo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1340 days.

(21) Appl. No.: 11/399,368

(22) Filed: Apr. 7, 2006

(65) Prior Publication Data

US 2006/0189662 A1    Aug. 24, 2006

Related U.S. Application Data

(63) Continuation of application No. PCT/JP2004/014646, filed on Oct. 5, 2004.

(30) Foreign Application Priority Data

Oct. 10, 2003  (JP) .................................. 2003-352491

(51) Int. Cl.
*A61K 9/00* (2006.01)

(52) U.S. Cl.
USPC .......................................... 424/400; 424/450

(58) Field of Classification Search
USPC ........................................................ 424/400
See application file for complete search history.

(56) References Cited

U.S. PATENT DOCUMENTS 5,599,528 A * 2/1997 Igaki ............................... 424/59

FOREIGN PATENT DOCUMENTS

| | | |
|---|---|---|
| CN | 1337227 A | 2/2002 |
| JP | 58-103325 A | 6/1983 |
| JP | 61-5011 A | 1/1986 |
| JP | 61-234920 A | 10/1986 |
| JP | 61-260860 A | 11/1986 |
| JP | 62-250941 A | 10/1987 |
| JP | 05219885 A * | 8/1993 |
| JP | 6-36862 A | 2/1994 |
| JP | 2000-212066 A | 8/2000 |
| JP | 2002-80347 A | 3/2002 |
| JP | 2002-80365 A | 3/2002 |
| WO | WO-02/24152 A2 | 3/2002 |

OTHER PUBLICATIONS

Brigelius-Flohé et al. Journal of the Federation of American Societies for Experimental Biology, 1999;13,1145-1155.*

* cited by examiner

*Primary Examiner* — James Rogers
(74) *Attorney, Agent, or Firm* — Birch, Stewart, Kolasch & Birch, LLP

(57) ABSTRACT

It is an object of the present invention to provide a liquid preparation which excels in stability with no occurrence of precipitates and lees even after long storage. The liquid preparation contains a lipophilic material, a sucrose fatty acid ester, a polyoxyethylene hydrogenated castor oil, a polyglycerin fatty acid ester, a polyol and water. Also provided are a pharmaceutical preparation, cosmetic preparation, food and drink which contain the liquid preparation.

10 Claims, No Drawings

LIQUID PREPARATION

CROSS-REFERENCE TO RELATED APPLICATIONS

This application is a Continuation of co-pending PCT International Application No. PCT/JP2004/014646 filed on Oct. 5, 2004, which designated the United States, and on which priority is claimed under 35 U.S.C. §120. This application also claims priority under 35 U.S.C. §119(a) on Patent Application No(s). 2003-352491 filed in Japan on Oct. 10, 2003. The entire contents of each of the above documents is hereby incorporated by reference.

BACKGROUND OF THE INVENTION

1. Field of the Invention

The present invention relates to a liquid preparation which contains lipophilic material that excels in storage stability and has no water-insoluble material (precipitates and lees) even after long storage.

2. Description of the Related Art

Many compounding techniques which arrange liquid medication, injections, cosmetics, etc. in a stable condition in which lipophilic materials are not separated over time have been proposed because lipophilic material in general is poorly-soluble in water and it is likely to separate over time even when dispersed uniformly in water at the beginning. Proposals relating to tocopherol exceptionally dominates among these proposals, for example, a solubilizing solution consisting of 3 ingredients, tocopherol, polyoxyethylene derivative of hydrogenated castor oil and polyglycerin fatty acid ester has been disclosed (Japanese Patent Application Laid-Open (JP-A) No. 61-5011). And a solubilizing composition which consist of 4 ingredients, tocopherol, sugars, sugar alcohols and polyglycerin unsaturated fatty acid ester is disclosed (JP-A No. 61-234920). A solubilizing solution consisting of 4 ingredients, tocopherol, water, polyol and polyglycerin fatty acid ester is also disclosed (JP-A No. 62-250941). Furthermore, a solubilizing composition consisting of 4 ingredients, tocopherol, sugars, sugar alcohols and polyglycerin fatty acid ester is disclosed (Japanese Patent Application Publication (JP-B) No. 06-36862).

However, there are problems with these proposals. Since extremely large amount of various additives must be added to the tocopherol, it does not match current consumers' needs which are likely to consume small amount of additives and moreover, it is impossible to prevent occurrence of precipitates and lees completely. In addition, it is unfavorable to use as a liquid medication because of strong undesirable taste typical for the additives.

At the same time, a solubilizing solution containing sucrose fatty acid ester as an additive is disclosed besides these proposals. For example, a coloring formulation in which lecithin and polyglycerin fatty acid ester are contained in a system which is emulsified and dispersed with sucrose fatty acid ester is disclosed (JP-A No. 58-103325). However, in this case, the effect of preventing precipitates and lees over time is not mentioned at all.

Moreover, a lipophilic material aqueous solution containing tocopherol, polyglycerin fatty acid ester, sucrose fatty acid ester, polyol and water is disclosed (JP-A No. 2000-212066). Furthermore, a solubilizing solution consisting of 4 ingredients of tocopherol, polyoxyethylene hydrogenated castor oil, polyglycerin fatty acid ester and sucrose fatty acid ester is disclosed (JP-A No. 2002-80365). However, in these cases, sucrose fatty acid ester is not necessary an essential ingredient and the effect of preventing precipitates and lees over time is not mentioned at all.

On the other hand, a liquid medication containing 5 ingredients of tocopherol acetate, polyoxyethylene hydrogenated castor oil, polyglycerin fatty acid ester, sucrose fatty acid ester and glycerin is disclosed (JP-A No. 2002-80347). In this disclosure, however, it is only intended to obtain appropriate dosability by preventing rusty taste originated from bivalent iron ion.

The liquid preparation in which the sucrose fatty acid ester is an essential ingredient and other ingredients are further optimized to prevent precipitates and lees highly effectively even after long storage, contributing to excellent stability and transparency, which is suitable for use in pharmaceutical preparation, cosmetic preparation, foods and drinks are not yet provided in the existing circumstances and the development is strongly desired.

SUMMARY OF THE INVENTION

The challenge of the present invention is to settle above existing issues and to achieve the following object. The object of the present invention is to provide a liquid preparation suitable for use in pharmaceutical preparations, cosmetic preparations, foods and drinks which is highly effective in preventing precipitates and lees even after long storage, contributing to excellent stability and transparency by containing sucrose fatty acid ester as an essential ingredient and further optimizing other ingredients.

The inventor has acquired the following knowledge after a dedicated investigation conducted by the inventor to settle above issues. It is a remarkable new knowledge that the deposition of tocopherol is prevented highly effectively even after long storage, contributing to excellent stability when, for the first time, 6 ingredients including sucrose fatty acid ester, tocopherol, polyoxyethylene hydrogenated castor oil, polyglycerin fatty acid ester, polyol and water are provided.

The present invention is based on the knowledge of the present inventor and the measures to settle above issues are the following.

A liquid preparation containing a lipophilic material, a sucrose fatty acid ester, a polyoxyethylene hydrogenated castor oil, a polyglycerin fatty acid ester, a polyol and water. In the liquid preparation as stated above, precipitates and lees are prevented highly effectively even after long storage through a synergic effect of these 6 ingredients, a lipophilic material, a sucrose fatty acid ester, a polyoxyethylene hydrogenated castor oil, a polyglycerin fatty acid ester, a polyol and water which are contained in the liquid preparation.

A manufacturing method of liquid preparation including mixing of a lipophilic material, a sucrose fatty acid ester, a polyoxyethylene hydrogenated castor oil, a polyglycerin fatty acid ester, a polyol and water, wherein the liquid preparation contains a lipophilic material, a sucrose fatty acid ester, a polyoxyethylene hydrogenated castor oil, a polyglycerin fatty acid ester, a polyol and water. In the manufacturing method of liquid preparation as stated above, the liquid preparation is manufactured by mixing a lipophilic material, a sucrose fatty acid ester, a polyoxyethylene hydrogenated castor oil, a polyglycerin fatty acid ester, a polyol and water.

A pharmaceutical preparation, cosmetic preparation, food and drink containing a liquid preparation, wherein the liquid preparation contains a lipophilic material, a sucrose fatty acid ester, a polyoxyethylene hydrogenated castor oil, a polyglycerin fatty acid ester, a polyol and water. The pharmaceutical preparations, cosmetic preparations, foods and drinks containing the liquid preparation exhibit excellent stability because precipitates and lees are prevented highly effectively even after long storage. It is therefore suitable for liquid medication such as various energy drinks.

By the present invention, it is possible to provide a liquid preparation in which precipitates and lees are prevented highly effectively even after long storage, contributing to excellent stability and transparency, which is suitable for use in pharmaceutical preparations, cosmetic preparations, foods and drinks.

DESCRIPTION OF THE PREFERRED EMBODIMENTS (Liquid Preparation)

The liquid preparation of the present invention contains a lipophilic material, a sucrose fatty acid ester, a polyoxyethylene hydrogenated castor oil, a polyglycerin fatty acid ester, a polyol and water (hereinafter may be referred to as "6 ingredients") and contains other ingredients accordingly.

-Lipophilic Material-

The lipophilic material is not particularly limited and may be selected accordingly. Examples include lipophilic vitamins such as vitamin A, β-carotene, vitamin D, vitamin E, vitamin K and the like, crotamiton, teprenone, and the like. These may be used alone or in combination. Of these, it is preferably vitamin A, vitamin D, vitamin E and vitamin K and more preferably vitamin E.

The vitamin E is not particularly limited and may be natural or synthetic product. Examples include α-tocopherol, β-tocopherol, γ-tocopherol, δ-tocopherol, α-tocotrienol, β-tocotrienol, γ-tocotrienol, δ-tocotrienol and derivatives of these. These may be any one of dl-, d- and l- forms and it is preferably d- and dl- forms and specific examples include d-α-tocopherol and dl-α-tocopherol. These may be used alone or in combination.

The derivatives are not particularly limited and may be selected accordingly. Examples include organic acid salt.

Examples of the organic acid salt include acetate, nicotinate and succinate and specific examples include d-α-tocopherol acetate and dl-α-tocopherol acetate. These may be used alone or in combination.

The vitamin A is not particularly limited and may be natural or synthetic product. Examples include retinol, retinal, carotene and retinoid.

The vitamin D is not particularly limited and may be selected accordingly. Examples include vitamin $D_1$, vitamin $D_2$ and vitamin $D_3$.

The vitamin K is not particularly limited and may be selected accordingly. Examples include vitamin $K_1$ and vitamin $K_2$.

The content of the lipophilic material is not particularly limited and may be selected accordingly. For example, it is preferably 3% by mass to 15% by mass and more preferably 5% by mass to 13% by mass.

-Sucrose Fatty Acid Ester-

The carbon number of the sucrose fatty acid ester is not particularly limited and may be selected accordingly. It is preferably 10 to 22 and more preferably 14 to 18, for example.

The sucrose fatty acid ester is not particularly limited and may be selected accordingly. Examples include sucrose stearate, sucrose palmitate, sucrose myristate, sucrose oleate, sucrose laurate, sucrose behenate and sucrose erucate. These may be used alone or in combination.

The content of the sucrose fatty acid ester is not particularly limited and may be selected accordingly. For example, it is preferably 0.3% by mass to 4% by mass and more preferably 0.5% by mass to 3.5% by mass relative to the lipophilic material.

-Polyoxyethylene Hydrogenated Castor Oil-

The additional mole number of ethylene oxide in the polyoxyethylene hydrogenated castor oil is not particularly limited and may be selected accordingly. For example, it is preferably 30 to 80 and more preferably 40 to 60.

The content of the polyoxyethylene hydrogenated castor oil is not particularly limited and may be selected accordingly. For example, it is preferably 30% by mass to 100% by mass and more preferably 40% by mass to 80% by mass relative to the lipophilic material in terms of high transparency.

-Polyglycerin Fatty Acid Ester-

The glycerin condensation of the polyglycerin fatty acid ester is not particularly limited and may be selected accordingly and it is preferably 2 to 10, for example.

The carbon number of the polyglycerin fatty acid ester is not particularly limited and may be selected accordingly. For example, it is preferably 10 to 22 and more preferably 14 to 18.

The polyglycerin fatty acid ester may be saturated fatty acid ester or unsaturated fatty acid ester and may be partially esterified or completely esterified.

The polyglycerin fatty acid ester is not particularly limited and may be selected accordingly. Examples include diglyceryl monostearate, diglyceryl monooleate, diglyceryl dioleate, diglyceryl monoisostearate, diglyceryl triisostearate, tetraglyceryl monostearate, tetraglyceryl monooleate, tetraglyceryl tristearate, tetraglyceryl pentastearate, tetraglyceryl pentaoleate, hexaglyceryl monolaurate, hexaglyceryl monomyristate, hexaglyceryl monostearate, hexaglyceryl monooleate, hexaglyceryl tristearate, hexaglyceryl tetrabehenate, hexaglyceryl pentastearate, hexaglyceryl pentaoleate, hexaglyceryl polyricinolate, decaglyceryl monolaurate, decaglyceryl monomyristate, decaglyceryl monostearate, decaglyceryl monoisostearate, decaglyceryl monooleate, decaglyceryl monolinoleate, decaglyceryl distearate, decaglyceryl diisostearate, decaglyceryl tristearate, decaglyceryl trioleate, decaglyceryl pentastearate, decaglyceryl pentahydroxystearate, decaglyceryl pentaisostearate, decaglyceryl pentaoleate, decaglyceryl heptastearate, decaglyceryl heptaoleate, decaglyceryl decastearate, decaglyceryl decaisostearate and decaglyceryl decaoleate. These may be used alone or in combination.

The content of the polyglycerin fatty acid ester is not particularly limited and may be selected accordingly. For example, it is preferably 10% by mass to 200% by mass and more preferably 30% by mass to 50% by mass.

-Polyol-

The polyol is not particularly limited and may be selected accordingly. Examples include glycerin, diglycerin, triglycerin, polyglycerin, propylene glycol, dipropylene glycol, 1,3-butylene glycol, ethylene glycol, polyethylene glycol, sorbitol, mannitol and xylitol. These may be used alone or in combination. Of these, glycerin is preferred.

The content of polyol is not particularly limited and may be selected accordingly. For example, it is preferably 30% by mass to 80% by mass and more preferably 40% by mass to 60% by mass.

-Other Ingredients-

Other ingredients are not particularly limited and may be selected from known additives. Examples include liquid paraffin, lipid and vegetable oil.

Examples of lipid include medium-chain fatty acid triglyceride and octyldecyl triglyceride.

Examples of vegetable oil include canola oil, olive oil, soybean oil, sesame oil and corn oil.

The liquid preparation of the present invention has an advantage in being able to prevent precipitates and lees highly effectively even after long storage by having sucrose fatty acid ester as an essential ingredient and by further containing lipophilic material, polyoxyethylene hydrogenated castor oil, polyglycerin fatty acid ester, polyol and water. Such effect can be achieved only by having 6 ingredients and it is particularly effective when sucrose fatty acid ester is contained and it is an extremely remarkable effect which had not been achieved by prior art. The liquid preparation of the present invention prevents deposition of water-insoluble material (precipitates and lees), contributing to excellent stability.

Therefore, the liquid preparation of the present invention is suitable for use in (1) liquid preparation of pharmaceutical preparations and medicated cosmetics such as energy drinks, liquids and solutions, syrups, rinse, elixirs and mouth washes, (2) pharmaceutical preparations, medicated cosmetics and compounding ingredient of cosmetics such as lotions, nasal drops, eardrops, transvaginal preparations, enteral preparations, aerosols, tinctures, ointments, liquids and solutions, jelly preparations and injections, (3) in addition to normal vehicle, pharmaceutical solids such as tablets, chewables, granules and capsules, (4) drinks such as soft drinks, carbonated drinks, milky drinks, fruit drinks and sports drinks; confectionaries, breads and processed meat products such as ham, bacon and sausage; processed oil and fat products such as margarine; processed marine products such as kelp, dried foods and boil dried foods and paste marine products such as fish sausage and steamed fish paste; noodles, fermented foods such as vinegar, soybean paste and soy sauce; sugars such as sugar, honey and starch; refrigerated and frozen foods, half-cooked and cooked foods, alcohol drinks, frozen desserts and foods such as enteral foods, health foods and specified health foods, (5) basic skin care such as perfume, eau de Cologne, bath agent, antiperspirant, tooth paste, mouth wash, lotions, milky lotions and cream, cosmetics such as soaps, skin cleansers, hair cosmetics and body-care products, and (6) feed for livestock, feed for fisheries and pet foods.

The content of the liquid preparation in pharmaceutical preparation, cosmetic preparation, foods and drinks is not particularly limited and may be selected accordingly. For example, it is preferably 0.001% by mass to 5% by mass.
(Manufacturing Method of Liquid Preparation, Pharmaceutical Preparation, Cosmetic Preparation, Foods and Drinks)

The manufacturing method of liquid preparation of the present invention include at least mixing of lipophilic material, sucrose fatty acid ester, polyoxyethylene hydrogenated castor oil, polyglycerin fatty acid ester, polyol and water. Meanwhile, the lipophilic material, sucrose fatty acid ester, polyoxyethylene hydrogenated castor oil, polyglycerin fatty acid ester and polyol are as described above.

The mixing can be performed by stirring with an agitator, homogenizer, homomixer, homojetter and the like in form of propeller, turbine, anchor and blender after mixing the lipophilic ingredients (tocopherol acetate, medium-chain fatty acid triglyceride, etc.) and aqueous ingredients (ingredients other than the above lipophilic ingredients) while heating at 70° C. to 100° C.

Hereinbelow, with referring to Examples and Comparative Examples, the invention is explained in detail and the following Examples and Comparative Examples should not be construed as limiting the scope of this invention.

Example 1

-Preparation of Liquid Preparation- 25 g of tocopherol acetate and 5 g of medium-chain fatty acid triglyceride (ODO manufactured by NOF Corp.) were stirred and mixed while heated at approximately 80° C. Furthermore, 12.5 g of decaglyceryl monostearate (NIKKOL Decaglyn 1-S manufactured by Nikko Chemicals Co., Ltd.), 15 g of polyoxyethylene hydrogenated castor oil (HCO-60 manufactured by Nikko Chemicals Co., LTd.), 2.5 g of sucrose fatty acid ester (Surfhope SE PHARMA J-1816 manufactured by Mitsubishi-Kagaku Foods Corp.), 137.5 g of concentrated glycerin and 52.5 g of purified water were heated at 80° C. and these are stirred and mixed. After these were mixed while pre-stirring by means of a stirrer, the mixture was then subjected to stirring for 10 minutes using a homo mixer (T. K. Robomix manufactured by PRIMIX Corporation) to obtain a homogeneous liquid preparation.

Examples 2 to 5 and Comparative Examples 1 and 2

Each liquid preparation was prepared in the same manner as in Example 1 following the prescription as shown in Table 1.

-Preparation of Energy Drink- 1 g of the liquid preparation of Example 1 was diluted with 100 ml of commercially available energy drink (A) which contains 20 mg of nicotinamide, 1 g of aminoethyl sulfonic acid, 5 mg of thiamine mononitrate, 5 mg of riboflavin sodium phosphate, 5 mg of pyridoxine hydrochloride, 100 mg of carnitine hydrochloride, 50 mg of inositol and 50 mg of anhydrous caffeine in one bottle of 100 ml as aqueous solution and a energy drink containing 100 mg of d-α-tocopherol acetate was prepared.

<Storage Stability Evaluation>

The liquid preparations of Examples 1 to 5 and Comparative Examples 1 and 2 were put in a transparent glass vial container of 30 ml and the container was put in a constant-temperature bath of 60° C. or 70° C. The vial container was taken out after 1 to 3 weeks, put in a constant-temperature bath of −5° C. and further left untouched for 0 to 2 weeks for an abusive test. The abusive test was conducted under the condition shown in Table 2. It was then taken out and returned to the room temperature and apparent condition was visually observed. Results are shown in Table 2.

TABLE 1

| | | Prescribed Amount (%) | | | | | | |
|---|---|---|---|---|---|---|---|---|
| | Ingredient | Ex. 1 | Ex. 2 | Ex. 3 | Ex. 4 | Ex. 5 | Comp. Ex. 1 | Comp. Ex. 2 |
| Prescription (%) | D-a-Tocopherol Acetate | 10 | 10 | 10 | 10 | 10 | 10 | 10 |
| | Medium-Chain Fatty Acid Triglyceride | 2 | 2 | 2 | 2 | 2 | 2 | 2 |

TABLE 1-continued

| Ingredient | Ex. 1 | Ex. 2 | Ex. 3 | Ex. 4 | Ex. 5 | Comp. Ex. 1 | Comp. Ex. 2 |
|---|---|---|---|---|---|---|---|
| Decaglyceryl Monostearate | 5 | 5 | 5 | 5 | 5 | 5 | 0 |
| Polyoxyethylene Hydrogenated Castor Oil 60 | 6 | 5.5 | 6 | 4 | 5 | 8.5 | 12 |
| Sucrose Fatty Acid Ester | 1 | 1 | 1 | 2 | 2 | 0 | 0 |
| Concentrated Glycerin | 55 | 55.5 | 55.5 | 55 | 55.5 | 55.5 | 55 |
| Purified Water | proper amount | proper amount | proper amount | proper amount | proper amount | proper amount | proper amount |
| Total | 100 | 100 | 100 | 100 | 100 | 100 | 100 |

TABLE 2

| Results from Abusive Test | Ex. 1 | Ex. 2 | Ex. 3 | Ex. 4 | Ex. 5 | Comp. Ex. 1 | Comp. Ex. 2 |
|---|---|---|---|---|---|---|---|
| 60° C. for 3 wks →−5° C. for 1 wk | A | A | A | A | A | E | E |
| 60° C. for 3 wks →−5° C. for 2 wks | A | A | A | A | A | E | E |
| 70° C. for 1 wk →−5° C. for 1 wk | A | A | A | A | A | E | F |
| 70° C. for 1 wk →−5° C. for 2 wks | A | A | A | A | A | F | F |
| 70° C. for 2 wks →−5° C. for 1 wk | A | B | B | A | B | E | F |
| 70° C. for 2 wks →−5° C. for 2 wks | B | A | A | A | A | F | F |
| 70° C. for 3 wks →−5° C. for 1 wk | B | A | A | A | B | E | F |
| 70° C. for 3 wks →−5° C. for 2 wks | B | B | A | B | A | E | F |
| 70° C. for 3 wks | A | A | A | A | A | F | F |

A: No visible deposition
B: Negligible amount of visible deposition which vanishes by oscillation →acceptable for commercialization
C: Tiny amount of visible deposition which vanishes by oscillation →acceptable for commercialization
D: Tiny amount of visible deposition which does not vanish by oscillation →unacceptable for commercialization
E: Small amount of visible deposition which does not vanish by oscillation →unacceptable for commercialization
F: Moderate amount or more of visible deposition which does not vanish by oscillation →unacceptable for commercialization Examples 6 to 12 and Comparative Examples 3 and 4

Each liquid preparation was prepared in the same manner as in Example 1 following the prescription as shown in Table 3. The storage stability was evaluated similarly to Example 1 and the results are shown in Table 4.

TABLE 3

| | Ingredient | Ex. 6 | Ex. 7 | Ex. 8 | Ex. 9 | Ex. 10 | Ex. 11 | Ex. 12 | Comp. Ex. 3 | Comp. Ex. 4 |
|---|---|---|---|---|---|---|---|---|---|---|
| Prescription (%) | D-a-Tocopherol Acetate | 10 | 10 | 10 | 10 | 10 | 10 | 10 | 10 | 10 |
| | Medium-Chain Fatty Acid Triglyceride | 1.5 | 0 | 1 | 1.5 | 2 | 2.5 | 3 | 2 | 2 |
| | Decaglyceryl Monostearate | 5.5 | 5 | 5.5 | 5.5 | 5 | 5.5 | 4 | 0 | 5 |
| | Polyoxyethylene Hydrogenated Castor Oil 60 | 3 | 4 | 3.5 | 3 | 7 | 4 | 5 | 12 | 8.5 |
| | Sucrose Fatty Acid Ester | 3.5 | 2 | 2.5 | 3 | 1 | 2 | 2 | 0 | 0 |
| | Concentrated Glycerin | 55 | 55 | 55 | 55 | 55 | 55 | 55 | 50 | 55 |
| | Purified Water | proper amount | proper amount | proper amount | proper amount | proper amount | proper amount | proper amount | proper amount | proper amount |
| | Total | 100 | 100 | 100 | 100 | 100 | 100 | 100 | 100 | 100 |

TABLE 4

| Results from Abusive Test | Ex. 6 | Ex. 7 | Ex. 8 | Ex. 9 | Ex. 10 | Ex. 11 | Ex. 12 | Comp. Ex. 3 | Comp. Ex. 4 |
|---|---|---|---|---|---|---|---|---|---|
| 70° C. for 1 wk →−5° C. for 1 wk | A | A | A | A | A | A | A | F | E |

A: No visible deposition
B: Negligible amount of visible deposition which vanishes by oscillation →acceptable for commercialization
C: Tiny amount of visible deposition which vanishes by oscillation →acceptable for commercialization
D: Tiny amount of visible deposition which does not vanish by oscillation →unacceptable for commercialization
E: Small amount of visible deposition which does not vanish by oscillation →unacceptable for commercialization
F: Moderate amount or more of visible deposition which does not vanish by oscillation →unacceptable for commercialization Since the liquid preparation of the present invention is highly effective in preventing precipitates and lees which contributes to excellent stability, it can be suitably used for (1) pharmaceutical preparation for internal application and liquid medication of medicated cosmetics such as energy drinks, liquids and solutions, syrups, rinse, elixirs, mouth washes and the like; (2) pharmaceutical preparations and medicated cosmetics for external use or compounding ingredient of cosmetics such as lotions, eye washes, nasal drops, eardrops, transvaginal preparations, enteral preparations and the like; and (3) in addition to normal vehicle, pharmaceutical solids such as tablets, chewables, granules, capsules and the like.

What is claimed is:

1. A liquid preparation comprising:
   a lipophilic material comprising at least one vitamin E;
   a sucrose fatty acid ester which is at least one member selected from the group consisting of sucrose stearate, sucrose palmitate, sucrose myristate, sucrose oleate, sucrose laurate, sucrose behenate, and sucrose erucate;
   30% by mass to 100% by mass, relative to said lipophilic material, of a polyoxyethylene hydrogenated castor oil;
   10% by mass to 200% by mass, relative to said lipophilic material, of a polyglycerin fatty acid ester;
   30% by mass to 80% by mass, relative to the total amount of the liquid preparation, of glycerin; and
   water.

2. The liquid preparation according to claim 1, wherein the vitamin E is selected from the group consisting of α-tocopherol, β-tocopherol, γ-tocopherol, δ-tocopherol, α-tocotrienol, β-tocotrienol, γ-tocotrienol, δ-tocotrienol and organic acid salts thereof.

3. The liquid preparation according to claim 2, wherein the organic acid salt is at least one selected from the group consisting of acetate, nicotinate and succinate.

4. The liquid preparation according to claim 1, wherein the content of the sucrose fatty acid ester relative to lipophilic material is 0.3% by mass to 4% by mass.

5. The liquid preparation according to claim 1, wherein the addition mole number of ethylene oxide in the polyoxyethylene hydrogenated castor oil is 30 to 80.

6. The liquid preparation according to claim 1, wherein the polyglycerin moiety in the polyglycerin fatty acid ester has a condensation degree of 2 to 10.

7. The liquid preparation according to claim 1, wherein the carbon number of the polyglycerin fatty acid ester is 10 to 22.

8. A method of manufacturing a liquid preparation comprising: mixing of at least one vitamin E, a sucrose fatty acid ester, a polyoxyethylene hydrogenated castor oil, a polyglycerin fatty acid ester, glycerin, and water, wherein the liquid preparation comprises: a lipophilic material comprising at least one vitamin E; a sucrose fatty acid ester which is at least one member selected from the group consisting of sucrose stearate, sucrose palmitate, sucrose myristate, sucrose oleate, sucrose laurate, sucrose behenate, and sucrose erucate; 30% by mass to 100% by mass, relative to said lipophilic material, of a polyoxyethylene hydrogenated castor oil; 10% by mass to 200% by mass, relative to said lipophilic material, of a polyglycerin fatty acid ester; 30% by mass to 80% by mass, relative to the total amount of the liquid preparation, of glycerin; and water.

9. A pharmaceutical preparation, cosmetic preparation, food, or drink comprising: a liquid preparation, wherein the liquid preparation comprises: a lipophilic material comprising at least one vitamin E; a sucrose fatty acid ester which is at least one member selected from the group consisting of sucrose stearate, sucrose palmitate, sucrose myristate, sucrose oleate, sucrose laurate, sucrose behenate, and sucrose erucate; 30% by mass to 100% by mass, relative to said lipophilic material, of a polyoxyethylene hydrogenated castor oil; 10% by mass to 200% by mass, relative to said lipophilic material, of a polyglycerin fatty acid ester; 30% by mass to 80% by mass, relative to the total amount of the liquid preparation, of glycerin; and water.

10. The pharmaceutical preparation, cosmetic preparation, food, or drink according to claim 9, wherein the liquid preparation is diluted with at least one member selected from the group consisting of water, buffer fluid and aqueous solution.

* * * * *